United States Patent [19]

Nauflett

[11] 4,154,658
[45] May 15, 1979

[54] PURIFICATION OF 1,1-DIMETHYL HYDRAZINE (UDMH) CONTAINING FORMALDEHYDE DIMETHYL HYDRAZONE

[75] Inventor: George W. Nauflett, Oxon Hill, Md.

[73] Assignee: The United States of America as represented by the Secretary of the Navy, Washington, D.C.

[21] Appl. No.: 921,926

[22] Filed: Jul. 3, 1978

[51] Int. Cl.$^2$ ............ B01D 3/36; C07C 109/02; C07C 109/14
[52] U.S. Cl. ............................... 203/59; 203/14; 203/35; 203/37; 203/43; 203/63; 203/64; 203/69; 203/70; 260/583 B
[58] Field of Search ............ 203/59, 63, 64, 69, 203/70, 34, 35, 43, 14, 37; 260/583 B

[56] References Cited

U.S. PATENT DOCUMENTS

| | | | |
|---|---|---|---|
| 2,676,911 | 4/1954 | Nicolaisen | 203/64 |
| 2,698,286 | 12/1954 | Bircher, Jr. | 203/12 |
| 2,806,851 | 9/1957 | Sisler et al. | 260/293 |
| 2,876,173 | 3/1959 | Nicolaisen | 203/14 |
| 2,963,407 | 12/1960 | Lewis | 203/12 |
| 3,012,948 | 12/1961 | Horvitz et al. | 203/59 |
| 3,098,017 | 7/1963 | Walter, Jr. et al. | 203/59 |
| 4,038,321 | 7/1977 | Thatcher et al. | 260/583 B |

Primary Examiner—Wilbur L. Bascomb, Jr.
Attorney, Agent, or Firm—R. S. Sciascia; A. L. Branning; H. B. Field

[57] ABSTRACT

The formaldehyde hydrazone of UDMH can be removed from an aqueous solution of UDMH by codistillation with a hydrocarbon or other solvent which is inert to both acidic or basis mediums. The solvent can then be recovered from the hydrazone solution by washing with an acid solution and the solvent can be reused.

6 Claims, No Drawings

PURIFICATION OF 1,1-DIMETHYL HYDRAZINE (UDMH) CONTAINING FORMALDEHYDE DIMETHYL HYDRAZONE

BACKGROUND OF THE INVENTION

This invention relates to a process for purifying unsymmetrical dimethyl hydrazine (UDMH). More specifically, hydrazone is extracted from a UDMH solution by distillation of the solution in the presence of a codistillation agent.

UDMH is employed primarily as a fuel for liquid propellant rockets and only relatively small amounts are used industrially for the preparation of agricultural chemicals. As a rocket fuel, UDMH is usually not used neat; it is mixed with other hydrazines or amines to obtain liquids of the proper freezing points and viscosities. These mixtures are used in several rockets and other propulsion devices throughout the Department of Defense and NASA. Unsymmetrical dimethyl hydrazine was originally prepared on a commercial scale by the Raschig method. The disadvantage of this process was that the UDMH has to be recovered from a dilute aqueous solution, a complicated and energy consuming operation. The increased demand for UDMH during the 1950's from an expanding aerospace industry generated the impetus for the development of a more economical manufacturing procedure. It is based on the catalytic hydrogenation of n,n-dimethylnitrosamine (DM-Nitroso). The method involved the catalytic reduction of n-nitrosodimethylamine which was prepared from dimethylamine and nitrous acid.

$$(CH_3)_2NH + HONO \rightarrow (CH_3)_2NNO + H_2O$$

$$(CH_3)_2NNO + (H) \xrightarrow{catalyst} (CH_3)_2NNH_2 + H_2O$$

UDMH was produced in large quantities by this method. In 1973, when DM-Nitroso was identified by the Occupational Safety and Health Administration (OSHA) as a known carcinogen, the production facility was shut down and modified to meet more stringent Environment Protection Agency (EPA) requirements. Other interesting innovations for the preparation of UDMH reported in the literature which do not involve a carcinogenic intermediate are shown below:

a. Sisler Gas Phase Chlorination of Ammonia:

$$2NH_3 + Cl_2 \rightarrow NH_2Cl + NH_4Cl$$

$$NH_2Cl + (CH_3)_2NH + NaOH \rightarrow (CH_3)_2NNH_2 + NaCl + H_2O$$

b. Alkylation of Hydrazine with an Alkyl Halide or Alkyl Sulfate:

$$2RCl + NH_2NH_2 \rightarrow R_2NNH_2 + 2HCl$$

c. 1,1-Dimethylurea Process:

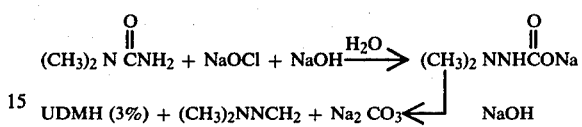

Both the Sisler and dimethylurea methods lead to the production of relatively large amounts of the formaldehyde hydrazone of UDMH because an oxidizing agent is used in the process. The oxidative interaction between $NH_2Cl$, NaOCl or other oxidizing ingredients and UDMH form the hydrazone as shown below:

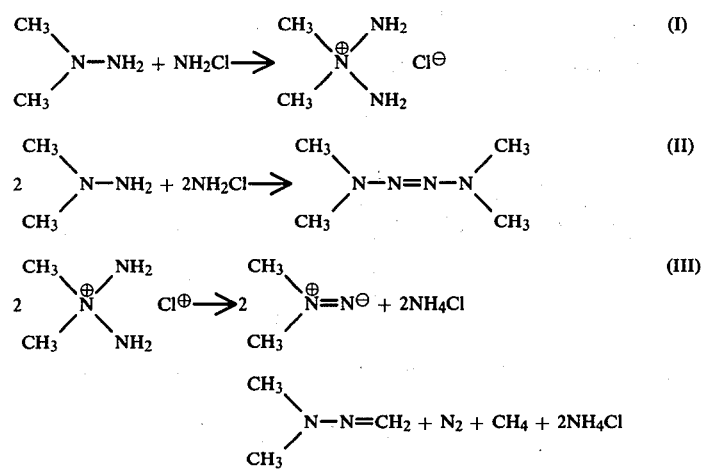

The second method does not appear to have any advantage over the abandoned Raschig method. A sizable research effort has been devoted to the Sisler route. Good yields of UDMH have been obtained with this method. However, for UDMH to be produced by this method on a commercial scale, the hydrazone must be removed from the UDMH or a method must be found to prevent its formation. The hydrazone cannot be removed from UDMH by simple distillation.

It is important to note that the three amine fuels, UDMH, monoethylhydrazine, and anhydrous hydrazine are each very dissimilar materials. The hydrazines are so named because of the nitrogen bonding within the molecule. The differences between the three hydrazines are attributable primarily to either the absence of or presence of one or two carbon atoms with bonds to adjacent hydrogen atoms. Unsymmetrical dimethyl hydrazine does not form an azeotrope with water while both of the other materials do form these azeotropes. There are numerous techniques available for dehydration of the azeotrope called hydrazine hydrate. U.S. Pat. Nos. 2,963,407 and 2,698,286 teach these techniques, however none of the prior art references teach the process for removing the hydrazone contaminant. In one of the above patents various alcohols are added to break the azeotrope form by allowing water to migrate up to the top of the column from where it can be removed as overhead product. In the other case, materials such as aniline are used in order to break the azeotrope. The difference between the dehydration techniques employed for anhydrous hydrazine and monomethylhydrazine are slight even though the major difference between these materials is that in one case for hydrazine there is a purely inorganic compound, while in the case of monomethylhydrazine there are carbon and hydrogen atoms involved within the molecule. In the case of separation by addition of a alcohol, the water is removed from the azeotrope by taking it up the column and removing water/alcohol as a product. This situation does not occur in the case of UDMH. The isopropanol treated within the present invention is utilized as a means for isolation between the water and UDMH thereby keeping both the water and the isopropanol in the distillation pot. Since unsymmetrical dimethyl hydrazine does not form an azeotrope but only has an affinity for water (as evidenced by a pinch point at the low concentrations of UDMH in water) it is necessary to treat UDMH differently as it really behaves differently than the other hydrazines.

The main problem encountered in trying to produce UDMH is that relatively high amounts (5–20%) of the formaldehyde hydrazone of UDMH is formed. Because of the similarity of the boiling points of the side product and UDMH, it is extremely difficult to effectively separate the two materials by distillation. Since the military specification for the rocket fuel calls for a minimum content of 98% UDMH, any material prepared in the above mentioned fashion is useless.

The prior art, included herein by reference, and defined in "Reaction of Chloramine with Anhydrous Primary and Secondary Amines," by G. M. Onnietonski, A. D. Kelmers, R. W. Shellmann, and H. H. Sisler, J.A.C.S. 78,3847 (1956) and in U.S. Pat. Nos. 2,806,851, 2,963,407 and 2,698,286, do not differentiate between UDMH and its formaldehyde hydrazone contaminant. The reason for this is that these test results were analyzed by oxidation with Potassium Iodate, and this system is unable to make that distinction.

SUMMARY OF THE INVENTION

Accordingly, there is provided by the present invention a process for extracting the formaldehyde hydrazone of UDMH from a solution containing unsymmetrical dimethyl hydrazine, the formaldehyde hydrazone of UDMH, water, dimethylamine, ammonia and other volatiles and non-volatiles, comprising the steps of adding a codistillation agent such as isopropanol, ethanol, ethylene glycol dimethyl ether, triethyleneamine, pentane, 2,2-dimethyl butane, 2,3 dimethyl butane, hexane(iso), hexane (n), heptane, and benzene so as to form a second solution and distilling the second solution at a temperature from about 50° C. to about 98° C. so as to codistill the formaldehyde hydrazone and the organic solvent.

OBJECTS OF THE PRESENT INVENTION

Therefore, it is an object of the present invention to provide a means for extracting formaldehyde hydrazone of UDMH from a UDMH solution containing, UDMH, the formaldehyde hydrazone of UDMH, dimethylamine (DMA), ammonia, and water.

Another object is to provide an economical method for extracting the formaldehyde hydrazone of UDMH from a UDMH solution.

Still a further object of the present invention is to allow the hydrocarbon solvent to be recovered from the hydrazone.

Other objects, advantages and novel features of the present invention will become apparent from the following detailed description of the invention.

DESCRIPTION OF THE PREFERRED EMBODIMENTS

UDMH manufacturing techniques currently employed yield a product which comprises UDMH, the formaldehyde hydrazone of UDMH, dimethylamine, ammonia, water, and other volatiles and non-volatiles. To-date, techniques used to obtain pure UDMH have either failed or have been economically impractical because the boiling points of the UDMH and the contaminent formaldehyde hydrazone of UDMH are very similar. Now, the contaminent formaldehyde hydrazone can efficiently and ecnomically be extracted from the UDMH solution by codistilling the contaminent with a codistillation agent.

To extract the formaldehyde hydrazone of UDMH from a solution containing unsymmetrical dimethyl hydrazine, the formaldehyde hydrazone of UDMH, dimethylamine, ammonia, water, and other volatiles and non-volatiles a codistillation agent is added to the above solution. Any hydrocarbon solvent which is immune to both acidic and basic attack can work for the above codistillation however, those of isopropanol, ethanol, ethylene glycol dimethyl ether, triethyleneamine, pentane, 2,2-dimethyl-butane, 2,3-dimethyl-butane, hexane (iso), hexane (n), heptane and benzene are preferred. The most preferred water soluble agent is isopropanol while the most preferred nonwater soluble agent is heptane. Although the codistillation agent can be added to the solution in amounts ranging from about 5 weight percent to about 50 weight percent, about 20 weight percent of the codistillation agent is preferred.

After the codistillation agent has been added to the UDMH solution, the resulting system is distilled at between about 50° C. and about 98° C. using a reflux type column. Actual distillation temperature will vary according to the organic solvent used as a codistillation agent and the percent of the agent in the hydrazone contaminated UDMH solution. Table I shows the boiling points and solubility of representative codistillation agents.

TABLE I

| Material | B.P. (°C.) | Solubility in Water |
|---|---|---|
| Ethylene glycol dimethyl ether | 85 | Yes |
| Triethylamine | 89 | Yes |
| Pentane | 36 | No |
| 2,2-Dimethyl-butane | 50 | No |
| 2,3-Dimethyl-butane | 58 | No |
| Hexane (iso) | 60 | No |
| Hexane (n) | 69 | No |
| Heptane | 98 | No |
| Ethanol | 80 (anhydrous) | Yes |
| Benzene | 80 | No |
| Isopropanol | 82 | Yes |

After completion of the first distillation step, sodium hydroxide is added to the UDMH solution and the UDMH caustic system is distilled to remove the remaining impurities from the UDMH. The use of caustic sodium hydroxide to separate UDMH from aqueous solutions is more specifically described in U.S. Pat. No. 2,876,173 to Nicolaisen, included herein by reference.

By way of illustration and not limitations, the following examples are described:

Table III

| | PURIFICATION OF UDMH CONTAINING HYDRAZONE | | | | | |
|---|---|---|---|---|---|---|
| Fraction | Weight (g) | B.P. (°C.) | UDMH (%) | Isopropanol (%) | Hydrazone (%) | Water (%) |
| I | 4 | 70 | 2 | 85 | 3 | 10 |
| II | 6 | 70–81 | 1 | 87 | 2 | 10 |
| III | 3.3 | 80 | 3 | 85 | 1.5 | 10 |
| IV | 8.3 | 80–82.5 | 10 | 81 | 1 | 8 |
| Distillation pot before NaOH addition | — | — | 22 | 2 | .2 | 75 |
| VI NaOH added | 4.6 | a | 97.5 | 1.5 | .5 | .5 |
| VII NaOH added | 1.7 | a | 97 | 2 | .5 | .5 |
| Oil layer from distillation pot | 8 | — | 15 | 8 | 1.3 | 46 | a UDMH condensed in reflux head at 57° C.

EXAMPLE I

A typical aqueous solution of UDMH containing unacceptable amounts of hydrazone has the following weight percent compositions:

UDMH: 16.5%
NH$_3$: 1.9%
DMA: 8.2%
Hydrazone: 2.3%
Water: 71.0%

To 100 ml, 95 g, of the above solutions, 25 ml, 19.6 g, of isopropanol was added. The isopropanol and hydrazone were codistilled between about 58° to 78° C. using a 1–10 reflux ratio. A Widmer column having approximately 30 height equivalent of a theoretical plates (HETH) was used for the codistillation. The ammonia, dimethylamine, and hydrazone came off with the isopropanol. After removal of the hydrazone, 40 g of sodium hydroxide was added and dissolved in the aqueous UDMH system. The remaining UDMH was distilled using a Vigreux (3 to 8) column; no reflux head was used. A second distillation using a Vigreux column was required to obtain specification grade UDMH. An 80% recovery of the UDMH was obtained in the first distillation. Shown in Table II are the boiling ranges of the various fractions and their approximate compositions. Redistillation of fraction I yielded specification grade UDMH.

Table II

| | PURIFICATION OF UDMH CONTAINING HYDRAZONE | | | | | |
|---|---|---|---|---|---|---|
| Fraction | Weight (g) | B.P. (°C.) | UDMH (%) | Isopropanol (%) | Hydrazone (%) | Water (%) |
| After NaOH added | | | | | | |
| I | 10 | 70–72 | 90 | 10 | 0.5 | 0 |
| II | 4 | 72 | 80 | 20 | 0.5 | 0 |
| aOil layer pot residue | 3 | — | 0.5 | 12 | 0.3 | 3 |
| bIa, redistilled fraction I of above | 6 | 65.5–66.5 | 98.5 | 0.5 | 0.5 | 0 |

EXAMPLE II

Isopropanol (25 ml, 19.6 g.) was added to the above UDMH mixture (100 ml, 95 g.) and refluxed with nitrogen flowing through the vapors; all of the ammonia and dimethylamine was removed in that manner. The isopropanol and hydrazone were codistilled at a boiling temperature of between about 70° to 90° C. using a 1 to 2 reflux ratio. A Widmer column (15 HETH) was used. Sodium hydroxide (80 g. of 50%) was added to the remaining solution in the pot and the UDMH was distilled. Shown in Table III are the boiling ranges and approximate compositions of the fractions.

The above example demonstrates that high quality UDMH (fractions VI and VII) can be obtained directly from the test mixture; additional NaOH is required to obtain specification grade UDMH. When isopropanol is used to remove the hydrazone by codistillation, the hydrazone is difficult to remove from it. The use of a water insoluble solvent (heptane) eliminates this problem.

EXAMPLE III

Removal of Hydrazone with Water Insoluble Components: Heptane (24 ml, 20 g.) was added to the above UDMH mixture (100 ml, 95 g.) and refluxed for one hour; all of the ammonia and dimethylamine was removed in that manner. The heptane and hydrazone were then codistilled at boiling temperatures up to about 80° C. Some of the water and UDMH (2.7 g.) distilled with the heptane. An inefficient Vigreux column with no reflux was used. The hydrazone was washed out of the heptane with 80% sulfuric acid. The UDMH was recovered by addition of sodium hydroxide pellets (40 g) to the distillation residue. A UDMH layer 20 g was separated and was not further purified. Shown below in Table IV are the anaylses by gas chromatography of UDMH distilled with heptane and pentane. The compositions given for the distillate are not as precise as those for the pot residues.

Table IV

Analyses of UDMH Distilled with Heptane and Pentane

| | Heptane | | | Pentane |
|---|---|---|---|---|
| | Pot Residue | Distillate | | Pot Residue |
| | | Heptane Layer | Water Layer | |
| | % | | | % |
| UDMH | 77 | 3 | 57 | 89.6 |
| Hydrazone | 0 | 3 | 7 | 0.5 |
| Water | 19 | 3 | 36 | 9.9 |
| Heptane | 4 | 91 | 1 | — |

Table IV-continued

| Analyses of UDMH Distilled with Heptane and Pentane | | | |
|---|---|---|---|
| | Heptane | | Pentane |
| | Distillate | | |
| Pot Residue | Heptane Layer | Water Layer | Pot Residue |
| % | | | % |
| Pentane | — | — | 0 |

The UDMH contained 0 and 0.5% hydrazone respectively where heptane or pentane was used.

The hydrazone is removed from the water insoluble solvents (heptane, etc.) by washing it with an acid. The heptane used in the above experiment contained no detectable hydrazone after an acid wash.

1. $(CH_3)_2 NN=CH_2$ (heptane solution) + $H_2SO_4 + H_2O \rightarrow [(CH_3)_2 NH_2]_2 H_2SO_4 + CH_2O$
2. Distill $CH_2O + H_2O$
3. $[(CH_3)_2 NH_2]_2 \cdot H_2SO_4 + NaOH \rightarrow (CH_3)_2 NNH_2 + Na_2SO_4$ What is new and desired to be secured by Letters Patent of the United States is:

1. A process for extracting the formaldehyde hydrazone of unsymmetrical dimethyl hydrazine from a solution containing unsymmetrical dimethyl hydrazine, water, the formaldehyde hydrazone of UDMH, dimethylamine, ammonia, and other volatiles and non-volatiles, comprises the steps of:

adding a codistillation agent selected from the group consisting of isopropanol, ethanol, ethylene glycol dimethyl ether, triethyleneamine, pentane, 2,2-dimethyl-butane, 2,3-dimethyl-butane, hexane (iso), hexane (n), heptane, and benzene to form a second solution; and distilling said second solution at a temperature from about 50° C. to about 98° C., so as to distill off the formaldehyde hydrazone of UDMH with the codistillation agent.

2. The process of claim 1 wherein said codistillation agents are selected from the group consisting of isopropanol, ethanol, triethylamine, and ethylene glycol dimethyl ether.

3. The process of claim 2 wherein said codistillation agent is isopropanol.

4. The process of claim 1 wherein said codistillation agents are selected from the group consisting of 2,2-dimethyl-butane, 2,3-dimethylbutane, pentane, hexane (iso), hexane (n), heptane, and benzene.

5. The process of claim 4 wherein said codistillation agent is selected from the group consisting of pentane and heptane.

6. The process of claim 5 wherein said codistillation agent is heptane.

* * * * *